(12) United States Patent
Tian

(10) Patent No.: US 9,700,667 B2
(45) Date of Patent: Jul. 11, 2017

(54) INTELLIGENT INFUSION PUMP

(71) Applicant: SHENZHEN WANJUYUAN TECHNOLOGY CO., LTD., Shenzhen, Guangdong (CN)

(72) Inventor: Wanbao Tian, Guangdong (CN)

(73) Assignee: SHENZHEN WANJUYUAN TECHNOLOGY CO., LTD., Shenzhen, Guangdong (CN)

( * ) Notice: Subject to any disclaimer, the term of this patent is extended or adjusted under 35 U.S.C. 154(b) by 75 days.

(21) Appl. No.: 14/371,171

(22) PCT Filed: Dec. 10, 2012

(86) PCT No.: PCT/CN2012/086291
§ 371 (c)(1),
(2) Date: Jul. 8, 2014

(87) PCT Pub. No.: WO2014/048036
PCT Pub. Date: Apr. 3, 2014

(65) Prior Publication Data
US 2014/0330205 A1    Nov. 6, 2014

(30) Foreign Application Priority Data

Sep. 27, 2012 (CN) .......................... 2012 1 0368782

(51) Int. Cl.
*A61M 1/00*   (2006.01)
*A61M 5/142*  (2006.01)
(Continued)

(52) U.S. Cl.
CPC .......... *A61M 5/142* (2013.01); *A61M 5/1411* (2013.01); *A61M 5/155* (2013.01);
(Continued)

(58) Field of Classification Search
CPC .... A61M 5/142; A61M 5/1411; A61M 5/155; A61M 5/16822; A61M 2205/07; A61M 2005/14208
(Continued)

(56) References Cited

U.S. PATENT DOCUMENTS 4,978,335 A * 12/1990 Arthur, III .......... A61M 5/1456
                                                      128/DIG. 1
5,899,665 A *  5/1999 Makino ............... A61M 5/1689
                                                         417/18
(Continued)

FOREIGN PATENT DOCUMENTS

CN    2221418    3/1996
CN    2568198    8/2003
(Continued)

OTHER PUBLICATIONS

Yang, Linsheng. Machine Translation of CN 2620547 (Description Only). Jun. 16, 2005. Translated Nov. 6, 2015.*
(Continued)

*Primary Examiner* — Edelmira Bosques
*Assistant Examiner* — Leah Swanson
(74) *Attorney, Agent, or Firm* — Rankin, Hill & Clark LLP

(57) ABSTRACT

An intelligent infusion pump includes a housing; a control circuit board; an input and display device; and a support base mounted on the housing to support a dropping bottle. The housing has an air cleaning device that communicates with an air inlet of an air pump of a motor pump assembly. An air outlet of the air pump of the motor pump assembly is connected with a seal joint via an air pipe with an air check valve. An air pressure sensor is mounted between the air check valve and the seal joint. The housing is further provided with an infusion flow control mechanism and a
(Continued)

power supply device. An infrared detection head is placed under the support base.

1 Claim, 3 Drawing Sheets

(51) Int. Cl.
*A61M 5/14* (2006.01)
*A61M 5/155* (2006.01)
*A61M 5/165* (2006.01)

(52) U.S. Cl.
CPC . *A61M 2005/1655* (2013.01); *A61M 2205/18* (2013.01); *A61M 2205/3331* (2013.01); *A61M 2205/50* (2013.01); *A61M 2205/502* (2013.01); *A61M 2205/507* (2013.01); *A61M 2205/6063* (2013.01)

(58) Field of Classification Search
USPC ........................................................ 604/151
See application file for complete search history.

(56) References Cited

U.S. PATENT DOCUMENTS

| | | | | |
|---|---|---|---|---|
| 6,036,668 A | * | 3/2000 | Mathis | A61M 1/28 604/29 |
| 6,790,198 B1 | * | 9/2004 | White | A61M 5/142 604/151 |
| 2008/0319391 A1 | * | 12/2008 | Jackson | A61J 15/0076 604/142 |
| 2009/0227855 A1 | | 9/2009 | Hill et al. | |

FOREIGN PATENT DOCUMENTS

| | | |
|---|---|---|
| CN | 2620547 | 6/2004 |
| CN | 101653628 | 2/2010 |

OTHER PUBLICATIONS

Zhao, Ming. Machine Translation of CN 101653628 (Description Only). Feb. 24, 2010. Translated Nov. 6, 2015.*
International Search Report of PCT/CN2012/086291 dated Feb. 7, 2013.

\* cited by examiner

INTELLIGENT INFUSION PUMP

BACKGROUND OF THE INVENTION

1. Technical Field

The present invention relates to the field of medical infusion devices, and more particularly, to an infusion device that can achieve accurate and continuous infusion when being used in a hospital for constant rate intravenous drug infusion to painful patients.

2. Description of Related Art

Doctors often use infusion methods to treat painful patients. Most existing infusion pumps are products manufactured by foreign technologies of the last century, and they generally copy foreign products directly and almost have no innovation. An existing infusion pump mainly includes a single chip computer control unit, a panel and key unit, a liquid crystal display unit, and a peristaltic extrusion unit. The peristaltic extrusion unit serves as a power unit of the infusion pump, that is, it generates mechanical peristalses to continuously compress infusion tubes and thereby make liquid medicine be output. However, the infusion tubes must be expensive special PVC tubes, otherwise they are unable to use. Common disposable infusion tubes are prone to deform or rupture when being continuously compressed, which does not only affect the infusion precision but also bring security risks to the infusion work. Furthermore, the existing infusion pump needs complicated operations and cannot be moved freely, and thus it is inconvenient to use.

How to design a convenient, safe, efficient, high-quality and inexpensive medical infusion device is an urgent technical problem to be solved in the industry.

BRIEF SUMMARY OF THE INVENTION

To solve the above-described technical problem, the present invention provides a convenient, safe, efficient, high-quality and inexpensive medical intelligent infusion pump.

The intelligent infusion pump provided by the present invention comprises: a housing; a control circuit board mounted in a lower part of the interior of the housing; an input and display device mounted at a side of the housing; and a support base mounted on an upper portion of a front surface of the housing and configured to support a dropping bottle; wherein, a back of the housing is provided with an air cleaning device, an air inlet of the air cleaning device is arranged outwardly, and an air outlet of the air cleaning device is arranged inwardly and communicates with an air inlet of an air pump of a motor pump assembly; an air outlet of the air pump of the motor pump assembly is connected with a seal joint mounted on the front surface of the housing via an air pipe with an air check valve, and an air pressure sensor is mounted on an air pipe connected between the air check valve and the seal joint of the housing; the interior of the housing is further provided with an infusion flow control mechanism and a power supply device, and an infrared detection head is mounted on the front surface of the housing and placed under the support base; and the control circuit board is electrically connected with the input and display device, the motor pump assembly, the air pressure sensor, the infusion flow control mechanism, the infrared detection head, and the power supply device.

Advantageously, a transparent window is mounted on a back of the support base mounted on the upper portion of the front surface of the housing and configured to support the dropping bottle, a scanner is mounted in the housing and electrically connected to the control circuit board, and a scanning head of the scanner is aligned with the transparent window on the support base.

Advantageously, the air cleaning device includes an air cleaning system and an ultraviolet sterilization system; the air cleaning system includes a protective cover, and a fiber filtering layer, a particle absorption layer, and a high-effect filtering layer orderly mounted in the protective cover; the ultraviolet sterilization system includes an ultraviolet sterilization chamber connected to the protective cover, an ultraviolet light source mounted in the ultraviolet sterilization chamber, and a conical ultraviolet light gathering cover, and the ultraviolet light gathering cover is connected with the air pipe of the air inlet of the air pump of the motor pump assembly via a port or directly.

Advantageously, the infusion flow control mechanism includes a micro motor electrically connected with the control circuit board, a reciprocating movement mechanism and a limit switch connected with the micro motor, and a back plate placed in a movement direction of the reciprocating movement mechanism.

Advantageously, a side of the housing is provided with a speaker electrically connected with the control circuit board. The power supply device is a chargeable battery.

Advantageously, an upper part of the housing is provided with a rotatable handle, and a part of the housing that is opposite to the input and display device defines a hook hole. A back of the housing is provided with an operation panel and a concave handle.

Advantageously, the infrared detection head is integrated with a support structure of an infusion observation bottle. An ultraviolet diode is mounted inside the seal joint.

In the present invention, the air pump is used to increase the pressure in the dropping bottle and thereby compensate the gravity pressure difference generated by the height reduction of the dropping bottle. The pressure difference is accurately calculated by the single chip computer and can be automatically adjusted according to the change of the pressure in the dropping bottle, so that the infusion process is stable and smooth. Since the air pump is used to provide the pressure and replaces the existing method of compressing infusion tubes by mechanical peristalses, using common infusion tubes can meet the requirements, and thus the use cost is reduced and the safety performance is improved. Furthermore, in the present invention, an air cleaning device is connected to the air inlet of the air pump; when the air pump sucks air in the atmosphere, the air cleaning device can apply sterilization and filtering to harmful bacteria and other dust and soot in the air at first, and thus the clean air entering the dropping bottle does not cause contamination of the liquid medicine, which may do harm to the safety of patients. The application of the air cleaning device in the infusion field and even the whole medical field will thoroughly eliminate and prevent harm caused by air contamination. Besides displaying infusion information by the input and display device, the infusion information can also be broadcast as voice information by the speaker, which is greatly convenient for medical workers, patients, or family members of patients to perform timely treatments. The present invention is a desktop design, which can be placed freely, and can perform infusion during movements. The present invention is convenient to use, safe, and inexpensive, and thus it will be welcomed by most medical workers and patients.

DETAILED DESCRIPTION OF THE INVENTION

Figure 1:
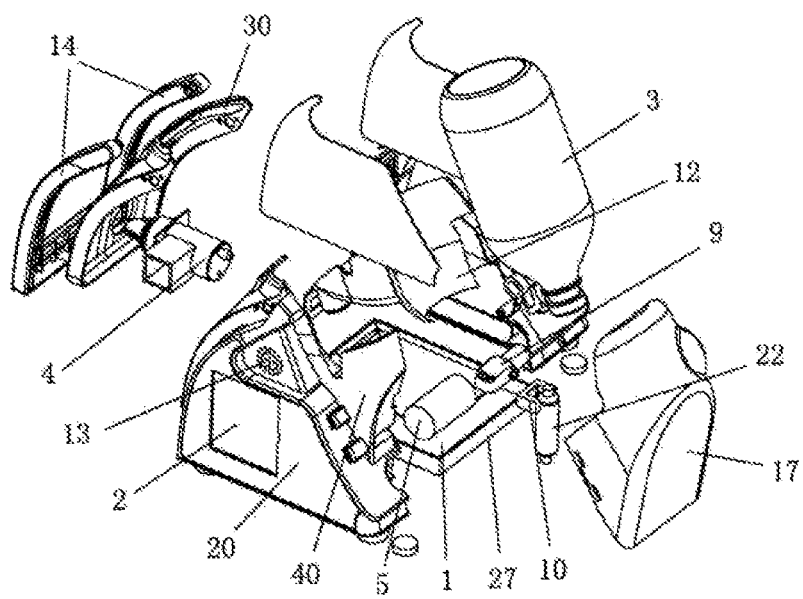
FIG. 1 is an exploded view of one embodiment of the present invention.
Figure 2:
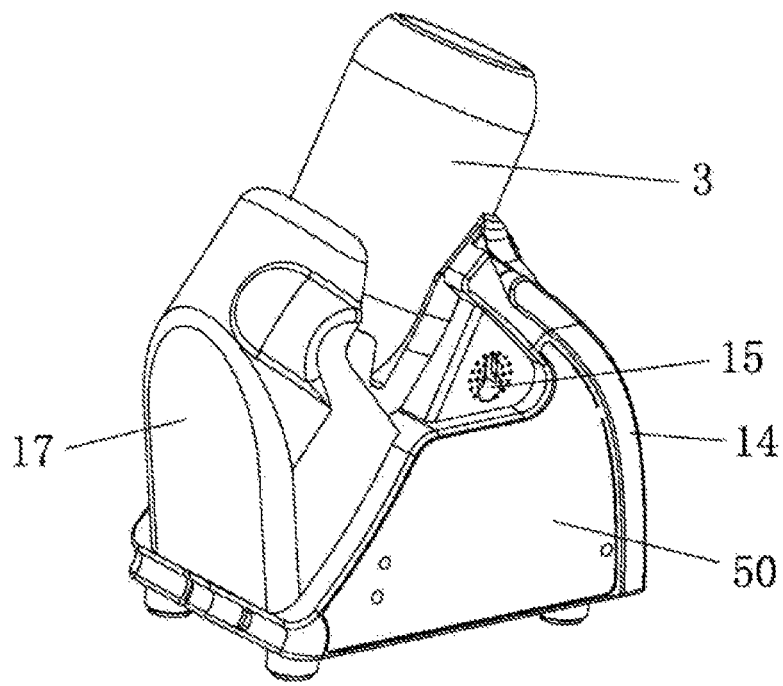
FIG. 2 is a front projection stereogram of the embodiment of the present invention.
Figure 3:
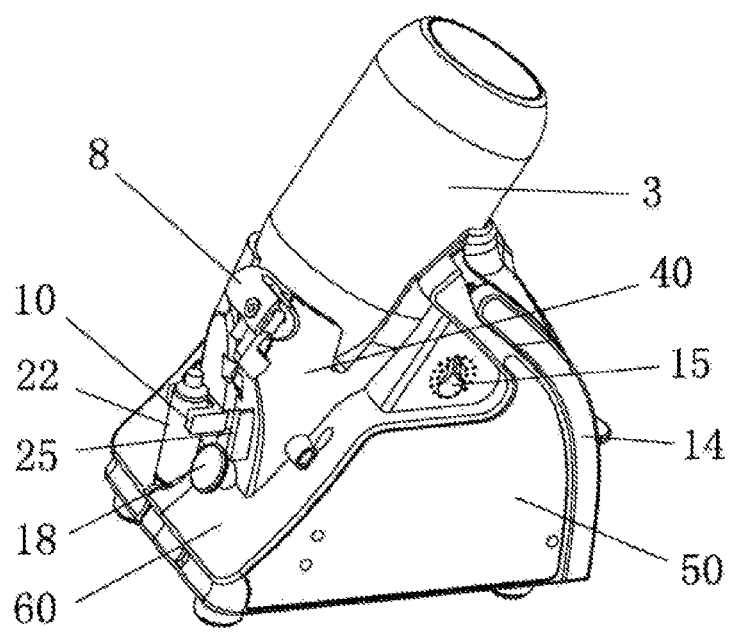
FIG. 3 is a front projection stereogram of the embodiment of the present invention, without a filter cover.
Figure 4:
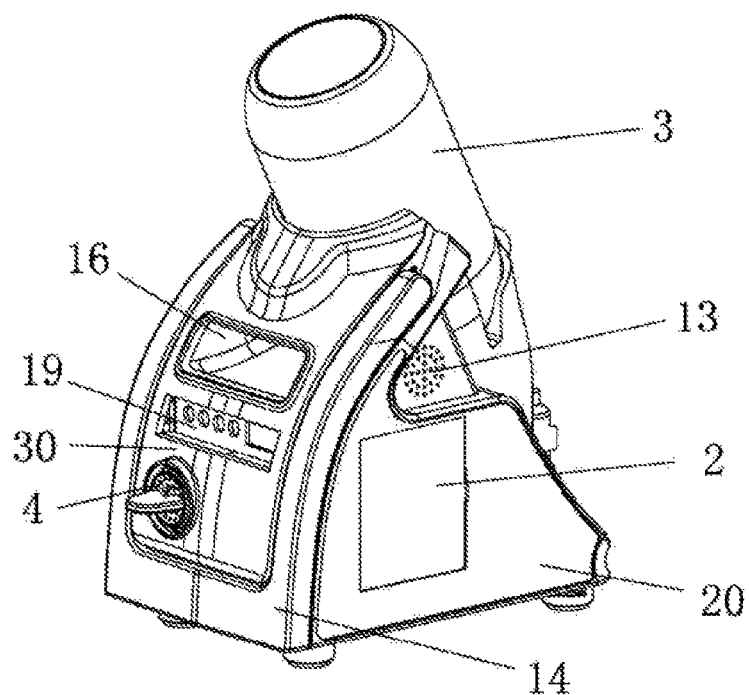
FIG. 4 is a back projection stereogram of the embodiment of the present invention.
Figure 5:
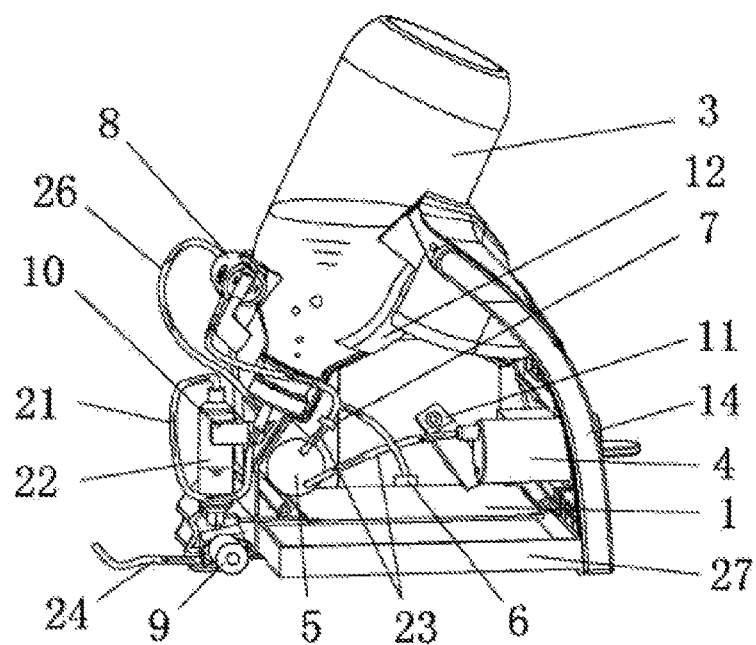
FIG. 5 is a schematic view of working principle of the present invention.
Figure 6:
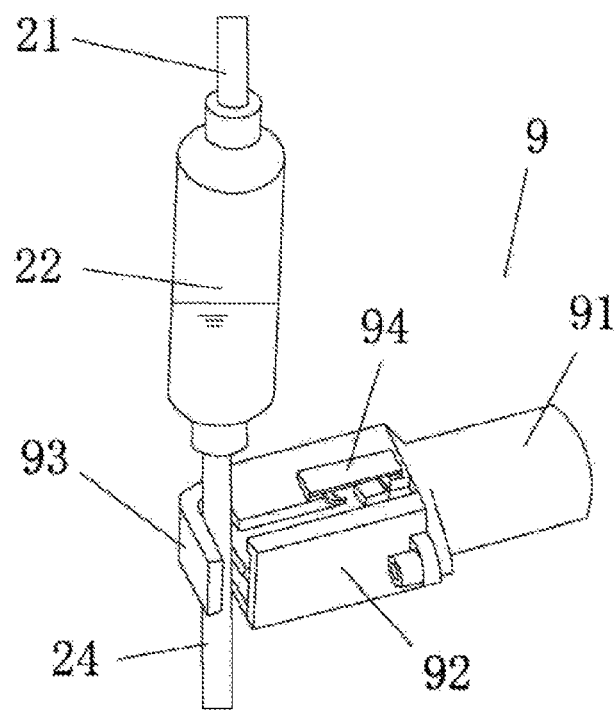
FIG. 6 is a schematic view of an infusion flow control mechanism of the present invention.

FIGS. 1-3 show a basic structure of one embodiment of the present invention. This embodiment provides an intelligent infusion pump, which comprises: a housing including a left casing 20, a right casing 50, a front casing 60, and a back casing 30; a support base configured to support a dropping bottle 3, wherein the support base is mounted on an upper portion of a front surface of the housing and includes left and right support elements 40, and a transparent window 12 is mounted on a back of the support base; an input and display device 2 mounted on the left casing 20; a speaker 13 mounted on the left casing 20; a hook hole 15 defined in the right casing 50; and a rotatable handle 14 hinged on an upper part of the housing. An infrared detection head 10 is mounted on the front surface of the housing and placed under the support base, and the infrared detection head 10 can be integrated with a support structure of an infusion observation bottle 22. A side of a casing of a support structure of the infrared detection head 10 is provided with an anti-bending guide slot 25 and an anti-bending guide pillar 18 which are configured to fix an infusion tube 21. An ultraviolet filter cover 17 configured to filter ultraviolet from external light is hinged on the front surface of the housing. When the ultraviolet filter cover 17 is opened, the dropping bottle 3 can be placed or replaced, and the infusion tube 21 can be fixed. When the ultraviolet filter cover 17 is closed, the infusion operation can be started. An air cleaning device 4 is mounted on a back of the housing, an air inlet of the air cleaning device 4 is arranged outwardly, and an air outlet of the air cleaning device 4 is arranged inwardly and communicates with an air inlet of an air pump of a motor pump assembly 5. Referring to FIG. 5, an air check valve 7 communicates with an air outlet of the air pump of the motor pump assembly 5, an air pipe 23 is connected to a seal joint 8 mounted on the front surface of the housing, and an air pressure sensor 6 is connected between the air check valve 7 and the air pipe 23. An ultraviolet diode (not shown) is mounted inside the seal joint 8. A scanner 11 is mounted in the housing, and a scanning head of the scanner 11 is aligned with the transparent window 12 on the back of the support base. A control circuit board 1, an infusion flow control mechanism 9, and a power supply device are mounted in a lower part of the interior of the housing. In this embodiment, the power supply device is a chargeable battery 27. The control circuit board 1 can be a single chip computer which is electrically connected with the input and display device 2, the air pressure sensor 6, the speaker 13, the motor pump assembly 5, the infusion flow control mechanism 9, the infrared detection head 10, the scanner 11, and the power supply device and can coordinate and control the work of these units or components according to work settings. The air cleaning device 4 includes an air cleaning system and an ultraviolet sterilization system (not shown). The air cleaning system can include a protective cover, and a fiber filtering layer, a particle absorption layer, and a high-effect filtering layer orderly mounted in the protective cover. The ultraviolet sterilization system can include an ultraviolet sterilization chamber connected to the protective cover, an ultraviolet light source mounted in the ultraviolet sterilization chamber, and a conical ultraviolet light gathering cover, and the ultraviolet light gathering cover is connected with the air pipe 23 of the air inlet of the air pump of the motor pump assembly 5 via a port or directly. As shown in FIG. 5 and FIG. 6, the infusion flow control mechanism 9 includes a micro motor 91 electrically connected with the control circuit board 1, a reciprocating movement mechanism 92 and a limit switch 94 connected with the micro motor 91, and a back plate 93 placed in a movement direction of the reciprocating movement mechanism 92. Another infusion tube 24 is mounted between the reciprocating movement mechanism 92 and the back plate 93. As shown in FIG. 4, the back casing 30 is further provided with a concave handle 16 and an operation panel 19. According to various requirements, the operation panel 19 can be provided with various components such as a power button, a speaker muter button, a bar code transformation switch, an information inquiry button, a sterilization switch, a power socket, a signal search button, and so on. The input and display device 2 can display various touch function keys, for example, a working key configured to perform work according to current settings after completion of setup, a pause key configured to stop infusion when being pressed, and a locking key configured to provide safety protection to the current settings. The input and display device 2 can further display the following setting items: the infusion rate (e.g., drops per minute); an add and subtract key configured to increase and decrease the infusion rate; quantitative selection keys configured to select specific infusing quantities for infusion, such as 50 ml, 100 ml, 150 ml, and 200 ml; a power status display area configured to display the power status and turn on a power indication lamp when the intelligent infusion pump is started, and drive an operation indication lamp to flash in an infusion process; and a power key configured to open the infusion flow control mechanism 9 and shut down the intelligent infusion pump after being pressed for 3-5 seconds. According to other requirements, the items displayed by the input and display device 2 can be regulated by the control circuit board 1.

As shown in FIG. 3 and FIG. 5, the present invention works as follows. The intelligent infusion pump is connected to a power supply; the dropping bottle 3, with a disposable infusion tube 21 inserted therein, is inversely placed on the support base; the disposable infusion tube 21 is turned a circle around the anti-bending guide pillar 18 and then received in the anti-bending guide slot 25 to prevent any bend of the disposable infusion tube 21 from blocking the infusion flow and further prevent the dropping bottle 3 from falling off during a movement. The infusion observation bottle 22 is fixed on the support structure thereof with the infrared detection head 10, and the infusion tube 24 is connected to a liquid outlet of the infusion observation bottle 22 and fixed between the back plate 93 and the reciprocating movement mechanism 92 of the infusion flow control mechanism 9 (referring to FIG. 6). Another air pipe 26 is connected to the dropping bottle 3, and a joint of the air pipe 26 is connected to the seal joint 8. Thus, the working settings, such as the infusion rate, the infusion quantity, and so on, are determined using the input and display device 2. If the working settings are not determined here, the intelligent infusion pump will work according to default settings, for example, an infusion rate of 30 drops per minute and no limited infusion quantity. When the working key is pressed once, the motor pump assembly 5 is started and pumps air into the infusion tubes to evacuate the infusion tubes. When the pause key is pressed, the evacuating operation is stopped, and infusion operations applied to human bodies, such as injection actions, can be performed. When the working key is pressed again, an infusion process is started. In the infusion process, the motor pump assembly 5 sucks air via the air cleaning device 4; the air is filtered and sterilized, and is then input to the air pump via the air pipe 23; the air pump compresses the air and outputs the compressed air to the seal joint 8 via another air pipe 23; and the compressed air is injected into dropping bottle 3 via the air pipe 26. When passing through the seal joint 8, the compressed air can be re-sterilized by ultraviolet sent from the ultraviolet diode mounted in the seal joint 8 to ensure the clean of the compressed air. Under the action of the compressed air, liquid medicine in the dropping bottle 3 enters the infusion observation bottle 22 via the infusion tube 21, and is infused to a patient via the infusion tube 24. The infrared detection head 10 is used to detect liquid drops in the infusion observation bottle 22 and send a detection signal to the control circuit board 1. The control circuit board 1 executes treatment measures according to the detection signal, that is, the control circuit board 1 sends instruction to the micro motor 91 of the infusion flow control mechanism 9, and thus the micro motor 91 drives the reciprocating movement mechanism 92 to press the infusion tube 24 onto the back plate 93 or release the infusion tube 24. The limit switch 94 mounted on the infusion flow control mechanism 9 can accurately control the moving distance of the reciprocating movement mechanism 92 and thus adjust the infusion flow freely. The air pressure sensor 6 is used to detect the air pressure in the air tubes and send a detection signal to the control circuit board 1. The control circuit board 1 executes treatment measures according to the detection signal, that is, the control circuit board 1 sends instruction to the motor pump assembly 5, and thus the air pump increases or maintains the pump pressure. The air check valve 7 is used to prevent the compressed air from flowing backwards.

The control circuit board 1 is a "brain" of the whole system, and is used to intelligently control and manage the whole system and process the detection signals. When the intelligent infusion pump malfunctions, the control circuit board 1 can give an alarm in time, stop the motor pump assembly 5 from working, and control the infusion flow control mechanism 9 to press the infusion tube 24 tightly and thereby stop the infusion, so that the safety of the patient can be ensured. If the present invention is used in a large-scaled medical institution, since the number of patients is great, the scanner 11 can be started to work. The scanner 11 scans a bar code on the dropping bottle 3 via the transparent window 12 on the support base of the dropping bottle 3, and inputs scanning information to the control circuit board 1 for comparison. If the liquid medicine in the dropping bottle 3 does not correspond to the infused patient, the control circuit board 1 stops the infusion operation promptly to ensure the safety of the patient. The present invention can be further provided with an alarm device. The control circuit board 1 can process the signals sensed by the sensors and generate alarm control signals accordingly, and the alarm device can respond the alarm control signals to remind persons to be careful and perform correct treatments in time. The alarm methods mainly include photoelectric alarm (e.g., light emitting diodes), sound alarm (e.g., speakers and buzzers), and so on.

In the input and display device 2, an input unit is used to set the infusion parameters, such as the infusion quantity, the infusion rate, and so on. A display unit is used to display the infusion parameters, the current working status, and so on. The display unit can be a segment-type liquid crystal display or a color liquid crystal display. The back casing 30 is provided with a 9V direct current power supply socket, which can be used to input working current to the intelligent infuse pump or charge the chargeable battery 27. The chargeable battery 27 is used to provide electric power to the intelligent infuse pump under the condition of no alternating current, so that the intelligent infuse pump can continue to work.

Since the air pump is used to provide the pressure and replaces the existing method of compressing infusion tubes by mechanical peristalses, using common infusion tubes can meet the requirements, and thus the use cost is reduced and the safety performance is improved. Furthermore, in the present invention, an air cleaning device is connected to the air inlet of the air pump, and thus the clean air entering the dropping bottle does not cause contamination of the liquid medicine, which may do harm to the safety of patients. The present invention can be placed freely, and can perform infusion during movements. The present invention is convenient to use, safe, and inexpensive, and thus it will be welcomed by most medical workers and patients.

The above specific embodiments are merely used to illustrate the structure of the present invention. In the spirit of the present invention, various modifications and changes may be made by one of ordinary skill in the art, and such modifications and changes are all included in the scope of the present invention.

The invention claimed is:

1. A method to transfuse utilizing an intelligent infusion pump, wherein the intelligent infusion pump comprises: a housing; a control circuit board mounted in a lower part of an interior of the housing; an input and display device mounted at a side of the housing; and a support base mounted on an upper portion of a front surface of the housing and configured to support a dropping bottle; wherein, a back of the housing is provided with an air cleaning device, an air inlet of the air cleaning device is arranged outwardly, and an air outlet of the air cleaning device is arranged inwardly and communicates with an air inlet of an air pump of a motor pump assembly; an air outlet of the air pump of the motor pump assembly is connected with a seal joint mounted on the front surface of the housing via a first air pipe with an air check valve, and an air pressure sensor is mounted on a second air pipe connected between the air check valve and the seal joint of the housing; the interior of the housing is further provided with an infusion flow control mechanism and a power supply device, and an infrared detection head is mounted on the front surface of the housing and placed under the support base; and the control circuit board is electrically connected with the input and display device, the motor pump assembly, the air pressure sensor, the infusion flow control mechanism, the infrared detection head, and the power supply device; wherein, a transparent window is mounted on a back of the support base, a scanner is mounted in the housing and electrically connected to the control circuit board, and a scanning head of the scanner is aligned with the transparent window; and wherein, the support base is configured to support the dropping bottle in such a way that the dropping bottle supported by the support base is used for infusion and a bar code on the dropping bottle supported by the support base is simultaneously aligned with the scanning head through the transparent window to be scanned through the transparent window by the scanning head; wherein, the infusion flow control mechanism includes a micro motor electrically connected with the control circuit board, a reciprocating movement mechanism and a limit switch connected with the micro motor, and a back plate placed in a movement direction of the reciprocating movement mechanism; the micro motor drives the reciprocating movement mechanism to press an infusion tube onto the back plate or release the infusion tube; an ultraviolet diode configured for sterilization is mounted inside the seal joint; wherein the method comprises: utilizing the power supply device to provide power to the intelligent infusion pump; placing the dropping bottle on the support base; fixing a infusion observation bottle on the support structure with the infrared detection head; connecting the infusion tube to a liquid outlet of the infusion observation bottle and fixing the infusion tube between the back plate and the reciprocating movement mechanism of the infusion flow control mechanism; connecting a third air pipe to the dropping bottle, and connecting a joint of the third air pipe to the seal joint; using the input and display device to determine infusion rate and infusion quantity; and infusion process which comprises: sucking air via the air cleaning device; filtering and sterilizing the air, and then inputting the air to the air pump via a fourth air pipe; compressing the air and outputting the compressed air to the seal joint via the third air pipe; and injecting the compressed air into the dropping bottle via the third air pipe; when passing through the seal joint, re-sterilizing the compressed air by ultraviolet sent from the ultraviolet diode mounted in the seal joint; wherein, under the action of the compressed air, liquid medicine in the dropping bottle enters the infusion observation bottle via the infusion tube, and is infused to a patient via the infusion tube; the infrared detection head is used to detect liquid drops in the infusion observation bottle and send a detection signal to the control circuit board; the control circuit board sends instruction to the micro motor of the infusion flow control mechanism, and thus the micro motor drives the reciprocating movement mechanism to press the infusion tube onto the back plate or release the infusion tube.

* * * * *